United States Patent [19]

Serimian et al.

[11] Patent Number: Plant 6,542

[45] Date of Patent: Jan. 17, 1989

[54] NECTARINE TREE, "MAY LION"

[76] Inventors: Donald M. Serimian, 2961 McCall Ave.; Lionel M. Serimian, 11310 E. Manning, both of Selma, Calif. 93662

[21] Appl. No.: 120,497

[22] Filed: Nov. 13, 1987

[51] Int. Cl.[4] ..... A01H 5/03

[52] U.S. Cl. ..... Plt./41

[58] Field of Search ..... Plt./41

*Primary Examiner*—Robert E. Bagwill

*Attorney, Agent, or Firm*—Worrel & Worrel

[57] ABSTRACT

A new and distinct variety of Nectarine Tree which is somewhat similar to the Arm King Nectarine Tree (U.S. Plant Pat. No. 2,943) and the Summer Grand Nectarine Tree (U.S. Plant Pat. No. 2,879) with which it is most closely related but which is distinguished therefrom and characterized as to novelty by producing fruit which are mature for commercial harvesting approximately May 18 through May 25 in the central part of the San Joaquin Valley of central California, and which further produces fruit which display a dark red skin color and which have a firm flesh and a clingstone nature.

1 Drawing Sheet

BACKGROUND OF THE NEW VARIETY

The present invention relates to a new and distinct variety of Nectarine Tree denominated varietally as "May Lion", and more particularly to a Nectarine Tree which is characterized by producing high quality, early season fruit which are ripe for commercial harvesting between May 18 and May 25 in the San Joaquin Valley of central California, and which is further distinguished as to novelty by producing fruit which have a large size, are clingstone by nature, and have a deep dark red color.

In a continuing effort to upgrade the quality of their fruit, the applicants have, from time to time, cross pollinated nectarine trees having desirable characteristics in the hope of developing a new and distinct variety of nectarine tree which could later be introduced to the market. In these labors to produce a new variety of nectarine tree, the applicants have routinely cross pollinated parent nectarine trees having known desirable traits and grown the resulting progeny to maturity, the applicants thereafter carefully studying the progeny's characteristics to determine whether or not a new variety of nectarine tree has been produced. The instant variety of nectarine tree "May Lion" was a product of this procedure.

The "May Lion" nectarine tree is noteworthy in that it produces fruit which are somewhat similar in physical characteristics to the Mayfire nectarine tree (unpatented), which produces fruit which were ripe for commercial harvesting during the first week in May; and the May Grand Nectarine Tree (U.S. Plant Pat. No. 2,794) which produces fruit which are ripe for commercial harvesting during the first week of June. The May Lion Nectarine Tree produces fruit which are distinguishable from the Mayfire and the May Grand nectarine trees in several improtant respects. When compared with the fruit produced by the Mayfire nectarine tree the May Lion Nectarine Tree produces fruit which are larger in size; possess a darker red skin coloration; and has a more favorable flavor and shape. Furthermore, when compared with the fruit produced by the May Grand Nectarine Tree, the May Lion Nectarine Tree produces fruit which have a darker red coloration; which mature for commecial harvesting approximately two weeks earlier than the May Grand Nectarine Tree; and further produces fruit which have a substantially globose shape as oppposed to the rather elongated shaped fruit produced by the May Grand Nectarine Tree.

ORIGIN AND ASEXUAL REPRODUCTION OF THE NEW VARIETY

The present variety of nectarine tree is the product of a successful cross pollination of an Armking Nectarine Tree (U.S. Plant Pat. No. 2,943) with a Summer Grand Nectarine Tree (U.S. Plant Pat. No. 2,879); the cross pollination being performed by the inventors in the Spring of 1983 at the applicants' orchard which is located at 11024 East Dinuba Avenue, Selma, Calif. Following the cross pollination, seeds were produced and the seeds were later germinated. Bud wood was later removed from the resulting plants in 1984 and was grafted onto test nectarine trees. The fruit produced were later examined to determine whether any desirable traits were present. When the superior qualities of the subject variety were detected and appreciated, the applicants later asexually reproduced the instant variety by budding the subject variety onto stock nectarine trees. This occurred at the applicants' same orchard in late 1985. The budding progeny were grown at the aforementioned orchard until it was determined that the new variety dependably and accurately reproduced the superior characteristics observed by the applicants in the original seedling.

BRIEF DESCRIPTION OF THE DRAWINGS

The drawing is a color photograph of a characteristic twig bearing typical leaves, four fruit showing their external coloration sufficiently mature for harvesting and shipment; and two fruit halved transversely of the suture plane to illustrate the flesh coloration and the stone characteristics, all of the subject variety.

DETAILED DESCRIPTION

Referring more specifically to the pomological details of this new and distinct variety of nectarine tree, the following has been observed under the ecological conditions prevailing at the orchard of the inventors which is located in Fresno County, Calif. All major color code designations are by reference to the "Dictionary of Color" by Maerz and Paul, Second Edition, published in 1950 or in the alternative by reference to the Inter-Society Color Council, National Bureau of Standards. Common color names are also employed occasionally.

TREE

Size: Average.

Vigor: Medium.

Figure: Variable; upright, to upright — spreading; the form and density of the subject variety is determined by pruning practices; the instant variety "May Lion" is hardy under typical San Joaquin Valley climatic conditions.

Trunk:

*Thickness.*—Variable; average to above average.

*Surface texture.*—Medium texture; a moderate amount of scarf skin is present.

*Bark color.*—Gray-brown, (7-E-9).

*Lenticels — size.*—Large.

*Lenticels — numbers.*—Numerous.

*Lenticels — generally.*—A corky callous tissue is present around the lenticel's opening.

*Color.*—Corky callous tissue — light brown, (13-J-9).

Branches:

*Size.*—One year old branches — average.

*Texture.*—One year old branches — medium.

*Color.*—Mature branches — variable, chestnut brown, (14-E-9) to a greenish-brown, (14-G-7).

*Lenticels — numbers.*—A moderate number of lenticels are present on the branches.

*Color — immature shoots.*—Light green (19-H-2).

*Texture — immature shoots.*—Smooth.

*Color — exposed shoots.*—This part of the plant is often tinged with red.

LEAVES

Size:

*Generally.*—Large.

*Average length.*—Approximately 189 mm.

*Average width.*—Approximately 44 mm.

Form: Lanceolate, the subject variety produces leaves which are rather narrow and which further are characterized by an acuminate leaf apex.

Color:

*Dorsal surface.*—Dark green, 24-L-5, (125. m. 01 G.).

*Ventral surface.*—A dull gray-green (21-H-3), 120. m. Y.G.).

Mid-vein:

*Generally.*—Prominent, approximately 1 mm in thickness at its center.

*Color.*—Light green (17-I-3).

Marginal form: Crenate; the crenations appear to be quite shallow; leaf margins are moderately undulate.

Petiole:

*Length.*—Average, approximately 11 to 13 mm.

*Thickness.*—Approximately 1.5 to 2.0 mm.

*Color.*—Light green, (19-H-3).

Leaf glands:

*Size.*—Average.

*Form.*—Mixed, often reniform.

*Location.*—The reniform type are located most often on the leaf margins, the globose type appear most frequently on the leaf petiole and on short stocks.

*Numbers.*—Variable, from four to seven; most commonly three to four glands are evident on the petiole and one to three leaf glands appear along the basal leaf margin.

*Pattern.*—Variable; alternate to nearly opposite positions.

*Color.*—Light green, (18-J-4).

*Texture.*—Shiny when young; the leaf glands darken and become brown with age.

Stipules:

*Numbers.*—Generally two can be found at the base of the leaf petiole.

*Size.*—Medium; approximately 10 to 11 mm. in length.

*Color.*—Light green, (18-J-5), when young. The stipules darken with age. Early deciduous.

FLOWERS

Blooming time: Mid-season to slightly late as compared to other common nectarine tree varieties.

Date of full bloom: Mar. 12, 1987 at Selma, Calif.

Flower size:

*Generally.*—Small.

*Diameter.*—Approximately 25 to 28 mm. when fully expanded. The flowers of the subject variety display a characteristic tendency not to open fully even when fully mature.

Bloom type: Non-showy form.

Bloom amount: Dense; the bloom density is above average as compared with other varieties.

FLOWER BUDS AND SCALES

Generally: The variety produces average sized buds.

Scale color: Gray-brown, (7-C-7).

Bud form: Conic.

Flowers:

*Numbers.*—The subject variety produces one to three flowers per node.

Petals:

*Size.*—Small.

*Length.*—Approximately 14 to 15 mm.

*Width.*—Approximately 10 to 11 mm.

*Form.*—Roughly oval, occasionally slightly ovate.

Claw:

*Form.*—Short and truncate. The petals of the subject variety display a characteristic tendency strongly to roll inwardly longitudinally.

Petals:

*Marginal form.*—Moderately undulate especially apically.

*Color.*—Light pink in the central portion of the petal, (1-E-2).

Color:

*Margin of petals.*—Variable, the marginal area of the petals has a distinctly darker pink or rose color, (1-H-4).

*Aging.*—The petals of the subject variety darken with age over the basal area, (1-H-3), however, this darkening does not continue over the remainder of the petal and a lightening of the color along the petal margin is sometimes evident at full maturity.

Pedicel:

*Length.*—Short, approximately 3 mm.

*Thickness.*—Approximately 1.5 mm.

*Color.*—Bright green, (17-H-6).

Nectaries:

*Color.*—Orange, (11-I-10); the nectaries of the subject variety darken slightly with age.

Anthers:

*Size.*—Average to above average.

*Color.*—Buff, (10-H-6). This color appears both ventrally and dorsally on same; a light red color (2-H-10) may be evident on the dorsal surface thereof.

Pollen:

*Quantity.*—Abundant.

*Color.*—Yellow, (10-L-3).

Stamens:

*Length.*—Approximately 11 to 15 mm. The length of the stamen is generally several millimeters shorter than the pistil.

*Color.*—Light pink, (1-C-1). The stamens of the subject variety darken with age and assume a pink-rose color (1-I-3).

Pistil:

*Length.*—Approximately 16 to 18 mm. The pistil of the subject variety extends generally 3 to 4 mm. above the anthers at full maturity.

*Color.*—Light green, (18-D-2).

*Texture.*—Glabrous.

FRUIT

Maturity when described: Ripe for commercial harvesting and shipment approximately May 18 through May 25 in Fresno County, Calif.

Size:

*Generally.*—Uniform and large; the large size of the subject variety is particularly noteworthy in view of its early date of maturity.

*Average diameter in the cheek plane.*—Approximately 62 mm.

*Average diameter in the suture plane.*—Approximately 61 mm.

*Average diameter in the axial plane.*—Approximately 59 mm.

Form: Uniform, and slightly asymmetrical, with one-half of the fruit becoming slightly larger than the other half.

Shape: Broadly ovate and nearly globose in its lateral aspect; somewhat elliptical in its axial aspect although some fruit can be found which are nearly globose.

Suture:

*Generally.*—Variable.

*Color.*—Variable, usually a very dark red-purple suture, (7-L-8), is evident.

*Position.*—The suture line is visible, and extends from the apex to a position near the base.

*Thickness.*—Approximately 1.5 to 2 mm.

*Appearance.*—The suture does not always appear as a continuous line and occasionally the center area of the suture does not exhibit the dark red-purple color (7-L-8). On these occasions, the suture line will assume the underlying blush color. The suture color generally appears darker toward the apical end of the fruit. The suture appears broadly but shallowly depressed over the apical shoulders ventrally.

Ventral surface:

*Shape.*—Rounded and smooth; very slightly lipped.

Stem cavity:

*Generally.*—Average depth; the variety has a moderately narrow cavity.

*Width.*—Approximately 20 to 23 mm.

*Length.*—Approximately 27 to 29 mm.

*Depth.*—Approximately 7 to 8 mm.

Base:

*Generally.*—Usually at a right angle to the fruit axis.

*Form.*—Rounded.

Apex:

*Shape.*—Rounded.

Pistil point:

*Generally.*—The pistil point is apical and very low; a slight depression appears on each side of the tip both dorsally and ventrally. A slight softening of the apex is detected with advancing maturity.

Stem:

*Length.*—Medium to short, approximately 7 to 8 mm.

*Thickness.*—Approximately 2.5 to 3 mm.

*Color.*—Light green, (19-I-4).

Skin:

*Thickness.*—Average.

*Flavor.*—Mild.

*Texture.*—Glabrous.

Tenacious to flesh: Yes.

Tendency to crack: Not observed.

Skin color: Bright red; this color covers approximately 75 to 95 percent of the fruit surface. The skin color is darkest over the apical end, dark red, (6-L-7), [16 d. Red]; a lighter cherry red color is evident over the remainder of the skin surface, (5-L-9).

Ground color: Where the ground color is visible through the blush an orange-red cast can be detected, (5-J-11).

Dots and speckling:

*Numbers.*—Numerous, especially over the apical shoulders.

*Ground color.*—Yellow, (18-I-1), although a slight tinge of green can be detected.

Flesh color: A uniform yellow, (10-J-2), no red coloration is seen in the flesh at commercial maturity.

Flesh texture: Firm and crisp at commercial maturity; softening of the flesh texture occurs with advancing age and the subject variety becomes moderately juicy with maturity.

Flesh fibers:

*Length.*—Average.

*Numbers.*—Medium.

*Texture.*—Fine and tender.

Ripening: The fruit ripens first at the apex.

Flavor: Rich, mildly acidic.

Aroma: Moderate.

Overall eating quality: Well above average.

STONE

Generally: Clingstone; No portion of the subject variety's flesh breaks free from the stone at commercial maturity.

Size:

*Generally.*—Medium.

*Stone length.*—Approximately 31 to 33 mm.

*Stone width.*—Approximately 24 to 26 mm.

*Stone breadth.*—Approximately 22 to 23 mm.

Fibers:

*Numbers.*—Numerous, and well attached.

Form: Roughly oval and slightly obovate.

Base:

*Shape.*—Slightly truncate; the base is slightly oblique with respect to the fruit axis.

Hilum:

*Size.*—Medium to small.

*Form.*—Narrow and oval.

Apex:

*Shape.*—Rounded, and having a very short tip.

Sides: Nearly equal and symmetrical.

Stone surface:

*Generally.*—Moderately pitted laterally on both sides of the stone with grooves and ridges being most prominent along the ventral surface and over the apical shoulders.

Ventral edge:

*Generally.*—Thick and deeply grooved. The grooves converge apically, and low wings are prominent at mid-suture.

Dorsal edge:

*Shape.*—Moderately wide with visible grooves appearing from the apex to the base.

Stone color: Buff, (10-D-5).

Tendency to split: Numerous internal splits are evident, occasionally a few splits are externally visible.

Use: Fresh market for both local and long distance shipping.

Keeping quality: Good.

Shipping quality: Unknown, although the firm and crisp flesh displayed at commercial maturity indicates that the variety should have noteworthy shipping characteristics.

Resistance to disease: No particular susceptibilities were noted.

Although the new variety of nectarine tree possesses the described characteristics as a result of the growing conditions prevailing in Fresno County, Calif., in the central part of the San Joaquin Valley, it is to be understood that variations in the usual magnitude and characteristics incident to growing conditions, fertilization, pruning and pest control are to be expected.

Having thus described and illustrated our new variety or nectarine tree, what is claimed as new and desired to be secured by Letters Patent is:

1. A new and distinct variety of Nectarine Tree substantially as illustrated and described which is remotely similar to the Armking Nectarine Tree (U.S. Plant Pat. No. 2,943) and the Summer Grand Nectarine Tree (U.S. Plant Pat. No. 2,879) from which it was derived as a cross pollinated offspring but from which it is distinguished therefrom and characterized as to novelty by producing fruit which are mature for commercial harvesting approximately May 18 through May 25 in Fresno County, Calif. and which additionally produces a large early season fruit having a dark red skin color and a superior globose shape, and which further has a flesh color which is a uniform clear yellow from the skin to the pit, the fruit of the subject variety having no red coloration in the flesh at commercial maturity.

* * * * *

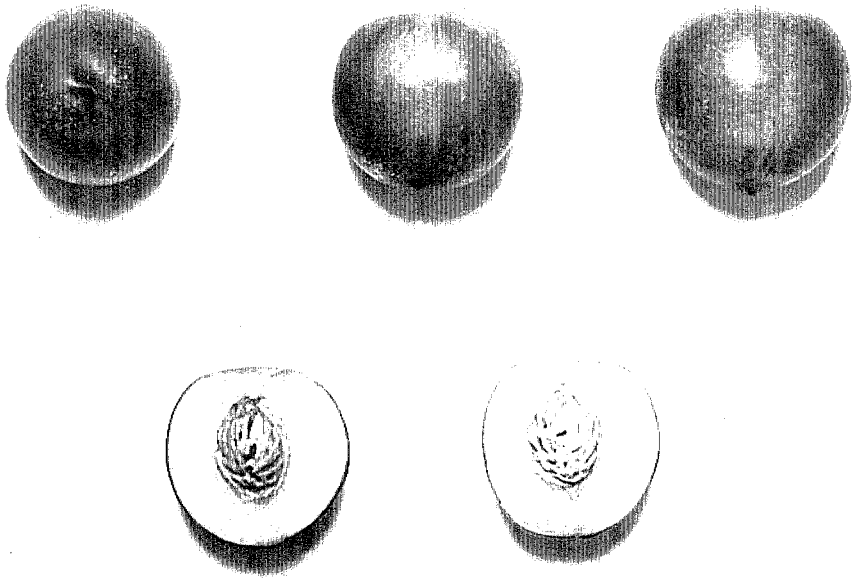
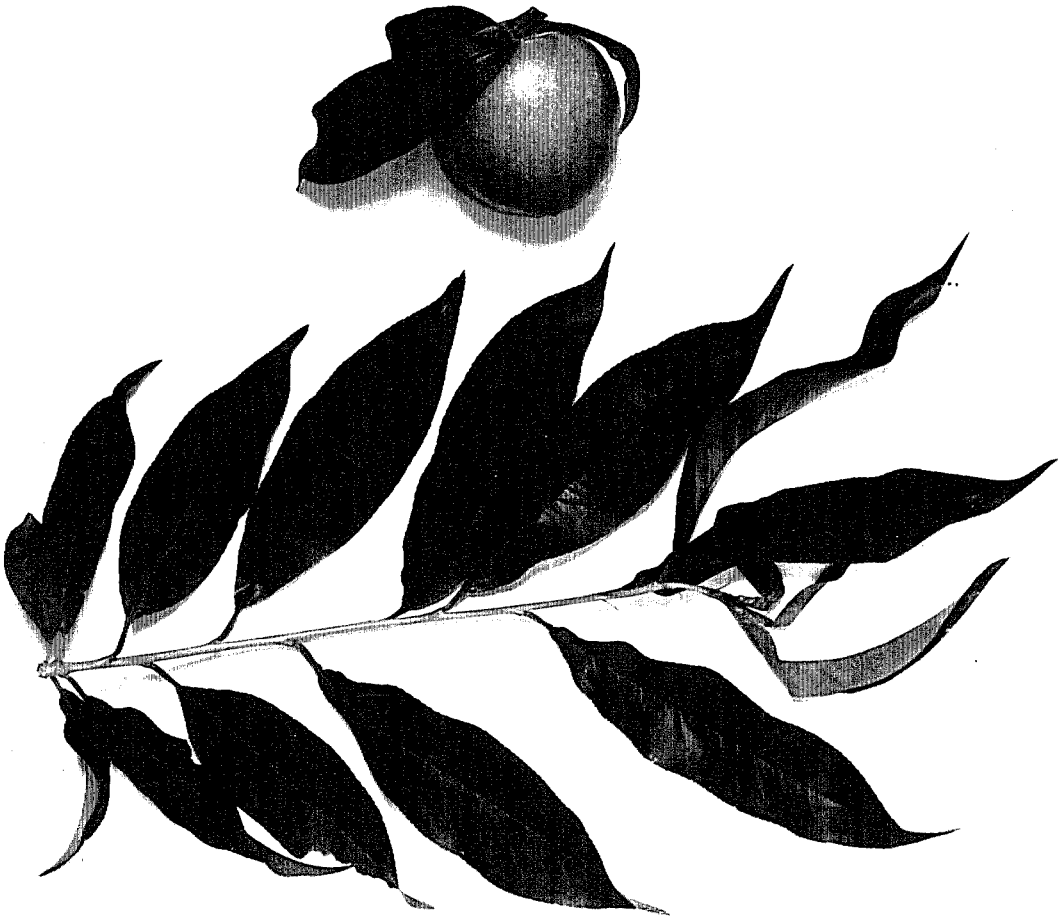

UNITED STATES PATENT AND TRADEMARK OFFICE

CERTIFICATE OF CORRECTION

PATENT NO. : PP 06,542

DATED : January 17, 1989

INVENTOR(S) : Lionel M. Serimian; Donald M. Serimian

It is certified that error appears in the above-identified patent and that said Letters Patent is hereby corrected as shown below:

Column 2, Line 25. Delete "budding" and insert ---budded---

Signed and Sealed this

Thirteenth Day of June, 1989

*Attest:*

*Attesting Officer*

DONALD J. QUIGG

*Commissioner of Patents and Trademarks*